United States Patent [19]

Puchelle et al.

[11] Patent Number: 5,420,116
[45] Date of Patent: May 30, 1995

[54] PHARMACEUTICAL COMPOSITIONS FOR THE TREATMENT OF DISORDERS OF THE RESPIRATORY TRACT

[75] Inventors: Edith Puchelle; Rachid Benali; Denis Pierrot; Sophie Girod, all of Reims Cedex; Jean-Marie Zahm, Reims; Aline Moreau, Paris, all of France

[73] Assignee: Synthelabo, Le Plessis Robinson, France

[21] Appl. No.: 894,328

[22] Filed: Jun. 4, 1992

[30] Foreign Application Priority Data

Jun. 5, 1991 [FR] France ................... 91 06783
Dec. 2, 1991 [FR] France ................... 91 14885

[51] Int. Cl.$^6$ ............... A61K 31/70; C07H 19/06
[52] U.S. Cl. ........................ 514/47; 514/45; 536/26.26
[58] Field of Search ............ 536/23, 24, 26, 27, 536/28, 29; 514/45, 46, 47, 48, 49, 50, 286, 255; 424/45, 46

[56] References Cited

U.S. PATENT DOCUMENTS 4,501,729 2/1985 Boucher et al. ................. 424/45
5,292,498 3/1994 Boucher, Jr. ..................... 424/45

FOREIGN PATENT DOCUMENTS

WO92/11016 7/1992 WIPO.

OTHER PUBLICATIONS

J. Cell Biol., 1990, 2: 107a.
Am. Rev. Resp. Dig., 1991, 143: A147.
Biol. Cell, 1990, 69:13a.
Eur. J. Cell, Biol., 1986, 40: 203–205.
The New England Journal of Medicine, 1991, vol. 325, No. 8 pp. 533–538.
British Journal of Pharmacology, 1991, vol. 103, No. 3, pp. 1649–1656.
"Breathing Easier", Endeavors, Research & Graduate Education at the Univ. of N. Carolina at Chapel Hill, Fall 1992 vol. X No. 1.
Drugs 43(4) 1992 431—439.
Arch Otorhinolaryngol (1988) 245:284–286.
Ceskoslovenska Otolaryngologic 38 (1989) 45–47.

Primary Examiner—Douglas W. Robinson
Assistant Examiner—A. Varma
Attorney, Agent, or Firm—Jacobson, Price, Holman & Stern

[57] ABSTRACT

Methods for treating disorders of the upper and lower airways, which disorders involve dehydration of the respiratory epithelium and hyperadhesion of mucus, using adenosine 5'-triphosphate disodium salt or uridine 5'-triphosphate, alone or in combination with amiloride.

1 Claim, No Drawings

PHARMACEUTICAL COMPOSITIONS FOR THE TREATMENT OF DISORDERS OF THE RESPIRATORY TRACT

The subject of the present invention is pharmaceutical compositions containing adenosine 5'-triphosphate disodium (ATP) or uridine 5'-triphosphate (UTP) which are useful for the treatment of disorders of the airways and cystic fibrosis.

Several cell types, especially epithelial cells, express receptors for extracellular ATP. The activation of these receptors is accompanied by modifications in the level of intracellular calcium, a mediator and regulator of multiple epithelial cell functions.

Consequently, micromolar concentrations of ATP are capable of causing rapid stimulation of the rate of ciliary flutterings of bronchial epithelial cells (Girard P. Kennedy J. Calcium regulation of ciliary activity in rabbit tracheal epithelial explants and outgrowth, Eur. J. Cell. Biol., 1986, 40: 203–205). This action seems to be linked to an increase of intracellular $Ca++$ (Villalon M., Hinds T. R. and Verdugo P. Intracellular $Ca++$ increases in respiratory ciliated cells following purinergic stimulation, J. Cell Biol., 1990, 2: 170a).

Recently, Professor Boucher's team (Stutts M. J., Chinet T., Boucher R. C., Receptors for extracellular ATP are tightly coupled to outward rectifying Cl-channels in human airway epithelium. Presented to the N. Am. CF Conference Arlington Oct. 1990) reported that extracellular ATP is capable of causing the opening of the chloride channels of the bronchial epithelium and of stimulating the intraluminal secretion of chloride. If, as mentioned by Boucher's team, extracellular ATP is capable of causing the opening of chloride channels, cultured epithelial cells should be capable of being stimulated by this extracellular ATP which, by actively increasing the intraluminal secretion of chloride, would increase the secretion of water.

To study the secretion of water by respiratory epithelial cells, the Applicant Company used a culture system in a two-compartment chamber which was recently developed (Dupuit F., Jacquot J., Benali R., Hinnrasky J. and Puchelle E., Polarised secretion of proteins by human tracheal gland cells cultured on a permeable substrate, Am. Rev. Resp. Dis., 1991, 143: A147).

Surface respiratory epithelial cells are obtained from human nasal polyps by enzymatic digestion according to a technique developed by the Applicant Company (Chevillard M., Hinnrasky J., Pierrot D., Zahm J. M., Klossek J. M., Puchelle E., Differentiation of human surface upper airway epithelial cells in primary culture on a floating collagen gel., Biol. Cell, 1990, 69: 13a). The respiratory epithelial cells are cultured on a semipermeable membrane coated with type I and II collagen in the presence of a serum-free culture medium supplemented with hormones and growth factor. The culture of cells on this semipermeable membrane permits access to the apical and basolateral cell surfaces separately.

The effect of ATP or UTP on water secretion is studied when the cells become confluent. The confluent state of the cells, which makes the cellular layer impermeable, is monitored by measuring the cellular resistance.

ATP or UTP is supplied to the cells by the apical compartment, in a volume of 100 μl of Ringer's solution, pH 7.4, at a final concentration of $10^{-4}M$. After incubating for two hours at 37° C., the variation of the volume of water in the apical compartment is evaluated by weighing. Volume losses due to the phenomena of dehydration under the experimental conditions were taken into account in this study.

Furthermore, the Applicant Company also studied the effects of ATP and UTP in the presence of amiloride.

The study is carried out after incubating the cells for 30 min in the presence or in the absence of amiloride at a concentration of $10^{-4}M$.

The results relating to the effects of ATP and UTP, in the presence or in the absence of amiloride, on the secretion of water by the cells obtained from the polyps of healthy individuals are very similar and are represented in Tables I and II below:

TABLE I

|  | Control | Control + amiloride | ATP* | ATP* + amiloride |
|---|---|---|---|---|
| Δ % of the initial volume | −1.26 ± 0.48 (n = 12) | +0.19 ± 0.48 (n = 7) | +1.65 ± 0.74 (n = 10) | +1.63 ± 0.77 (n = 7) |

TABLE II

|  | Control | Control + amiloride | UTP* | UTP* + amiloride |
|---|---|---|---|---|
| Δ % of the initial volume | −1.47 ± 0.51 (n = 8) | +0.31 ± 0.43 (n = 8) | +1.68 ± 0.52 (n = 8) | +1.69 ± 0.84 (n = 8) |

The values represent the mean ± standard deviation;
* $p < 0.001$
n = number of cultures.

The results obtained and set forth above show that amiloride alone blocks the reabsorption of water by surface respiratory epithelial cells. The effect of ATP or UTP alone (without preincubation with amiloride) on the respiratory epithelial cells leads to a significant increase ($p<0.001$) in the apical volume, and therefore to secretion of water by the cells.

Preincubation with amiloride does not significantly alter the effect of ATP or UTP on the secretion of water by the respiratory epithelial cells.

The results relating to the effect of ATP and UTP on the secretion of water by cells obtained from the polyps of individuals suffering from cystic fibrosis (CF) are represented in Tables III, IV and V below.

TABLE III

| | CFΔF 508 homozygote | | |
|---|---|---|---|---|
|  | Control | Control + amiloride | ATP | ATP + amiloride |
| Δ % of the initial volume | −1.90 ± 0.37 (n = 4) | −0.08 ± 0.40 (n = 4) | +0.93 ± 0.51 (n = 4) | +0.80 ± 0.60 (n = 4) |

TABLE IV

| | CF unidentified mutation | | |
|---|---|---|---|---|
|  | Control | Control + amiloride | ATP | ATP + amiloride |
| Δ % of the initial volume | −1.45 ± 0.66 (n = 6) | −0.64 ± 0.55 (n ~ 6) | +0.67 ± 0.27 (n = 6) | +0.82 ± 0.57 (n = 6) |

TABLE V

| | CFΔF 508 heterozygote | | | |
|---|---|---|---|---|
| | Control | Control + amiloride | UTP | UTP + amiloride |
| Δ % of the initial volume | −1.70 ± 1.05 (n = 5) | −0.38 ± 1.18 (n = 5) | +0.42 ± 0.24 (n = 5) | +1.08 ± 0.30 (n = 5) |

The results obtained show that for the cystic fibrosis (CF) respiratory epithelial cells, amiloride does not appear completely to block the reabsorption of water by these cells.

ATP or UTP, alone or in combination with amiloride, induces an increase in the apical volume and therefore secretion of water by the cells.

ATP and UTP, in the presence or in the absence of amiloride, are therefore capable of causing the opening of chloride channels at the level of the respiratory epithelium, of stimulating the secretion of chloride and water by this epithelium, and therefore of increasing hydration of the respiratory epithelium and of the mucus of the bronchi or the upper airways.

In patients whose respiratory epithelium is altered by various pathologies (cystic fibrosis, infections or inflammations of the upper and lower airways), the secretions are frequently dehydrated. Yet, during these pathologies, the elimination of the secretions essentially relies on cough clearance which depends on the adhesiveness of the mucus.

The decrease in the adhesiveness of the mucus is obtained in particular through its hydration. ATP, UTP or ATP+amiloride or UTP+amiloride combinations which can increase the hydration of the mucus, are therefore potential agents for the treatment of all bronchial or ORL disorders where dehydration of the epithelium and hyperadhesiveness of the mucus exist (inflammatory, infectious or allergic rhinitis, inflammatory, infectious, allergic or toxio bronchitis, or emphysema) and of cystic fibrosis.

The pharmaceutical compositions of the invention containing ATP, UTP, the ATP+amiloride combination or the UTP+amiloride combination, in combination with any appropriate excipient, may therefore be used for the treatment of these disorders. The pharmaceutical compositions of the invention may be administered by instillations or in the form of sprays for disorders in the ear-nose-throat field; they may be in the form of sprays or nebulisations for bronchial pathologies.

We claim:

1. A method of treating dehydration of the respiratory epithelium and hyperadhesion of mucus in a human, which comprises administering to said human a therapeutically effective amount of adenosine 5'-triphosphate disodium salt.

* * * * *